United States Patent
Vogt et al.

(10) Patent No.: US 9,770,355 B2
(45) Date of Patent: Sep. 26, 2017

(54) METHOD FOR PRODUCING A SPACER AND HOLLOW MOLD FOR PRODUCING A SPACER

(71) Applicant: HERAEUS MEDICAL GMBH, Wehrheim (DE)

(72) Inventors: Sebastian Vogt, Erfurt (DE); Hubert Büchner, Nürnberg (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 726 days.

(21) Appl. No.: 13/742,516

(22) Filed: Jan. 16, 2013

(65) Prior Publication Data

US 2013/0187310 A1    Jul. 25, 2013

(30) Foreign Application Priority Data

Jan. 17, 2012 (DE) .................. 10 2012 000 685

(51) Int. Cl.
*A61F 5/01* (2006.01)
*A61F 2/36* (2006.01)
(Continued)

(52) U.S. Cl.
CPC .............. *A61F 5/01* (2013.01); *A61F 2/36* (2013.01); *A61F 2002/30069* (2013.01);
(Continued)

(58) Field of Classification Search
CPC .. A61F 2002/30069; A61F 2002/30561; A61F 2002/30583; A61F 2002/30672;
(Continued)

(56) References Cited

U.S. PATENT DOCUMENTS 5,037,445 A     8/1991 Sander et al.
5,133,771 A *   7/1992 Duncan ............... A61F 2/30942
                                             264/DIG. 30
(Continued)

FOREIGN PATENT DOCUMENTS

CN      1596091 A     3/2005
CN   101 44 2963 A    5/2009
(Continued)

OTHER PUBLICATIONS

English translation of the First Office Action issued in corresponding application CN 201310016905.3 on Sep. 18, 2014.
(Continued)

*Primary Examiner* — Robert J Grun
(74) *Attorney, Agent, or Firm* — Norris McLaughlin & Marcus PA

(57) ABSTRACT

A method for producing a spacer for insertion as a placeholder for an articular endoprosthesis, whereby a cement is filled into a compressed hollow space of a flexible compressed hollow mold, whereby the flexible hollow mold is expanded by the cement flowing into it, and the cement is filled into the hollow mold until the hollow space is expanded to a final state, whereby the hollow space in its final state determines the shape of the spacer to be produced, and the cement is then cured in said hollow space, and the spacer produced from the cement is removed from the hollow mold after curing. The invention also relates to the hollow mold, which comprises the compressible hollow space, whereby the hollow mold comprises at least one filling opening through which cement can be filled into the hollow space.

8 Claims, 1 Drawing Sheet

(51) Int. Cl.
  *A61F 2/30* (2006.01)
  *A61F 2/46* (2006.01)
(52) U.S. Cl.
  CPC ............ *A61F 2002/30561* (2013.01); *A61F 2002/30583* (2013.01); *A61F 2002/30672* (2013.01); *A61F 2002/30677* (2013.01); *A61F 2002/4685* (2013.01); *A61F 2310/00353* (2013.01)
(58) Field of Classification Search
  CPC .... A61F 2002/30677; A61F 2002/4685; A61F 2310/00353; A61F 2/36; A61F 5/01
  USPC .......................................................... 264/313
  See application file for complete search history.

(56) References Cited

U.S. PATENT DOCUMENTS

| | | | |
|---|---|---|---|
| 6,361,731 | B1 | 3/2002 | Smith et al. |
| 7,572,295 | B2 | 8/2009 | Steinberg |
| 7,637,729 | B2 | 12/2009 | Hartman et al. |
| 8,814,946 | B2 | 8/2014 | Steinberg |
| 2005/0085915 | A1 | 4/2005 | Steinberg |
| 2007/0100447 | A1 | 5/2007 | Steinberg |
| 2007/0123991 | A1 | 5/2007 | Steinberg |
| 2007/0276491 | A1 | 11/2007 | Ahrens et al. |
| 2009/0069899 | A1 | 3/2009 | Klein |
| 2009/0157189 | A1 | 6/2009 | Hartman et al. |
| 2009/0259317 | A1 | 10/2009 | Steinberg |
| 2010/0070046 | A1 | 3/2010 | Steinberg |
| 2010/0185297 | A1 | 7/2010 | Steinberg |

FOREIGN PATENT DOCUMENTS

| | | |
|---|---|---|
| JP | 2009 538200 A | 11/2009 |
| WO | 98 51240 A1 | 11/1998 |

OTHER PUBLICATIONS

English translation of Notice of Reason for Rejection issued in corresponding Japanese application 2013-005402 dated Feb. 4, 2014.

Patent Examination Report No. 1 issued in corresponding Australian Patent Application No. 2013200129 on Apr. 23, 2014.

* cited by examiner

METHOD FOR PRODUCING A SPACER AND HOLLOW MOLD FOR PRODUCING A SPACER

This application claims priority of German Patent Application No. 10 2012 000 685.3, filed Jan. 17, 2012, the entire contents of which are incorporated herein by reference.

The invention relates to a method for producing a spacer for insertion as a placeholder for an articular endoprosthesis and to a hollow mold for producing a spacer for insertion as a placeholder for an articular endoprosthesis, in particular for implementing a method of said type.

Accordingly, the subject matters of the invention are a hollow mold or spacer casting mold for producing polymethylmethacrylate bone cement spacers designed to be temporary placeholders for two-stage revisions of infected total endoprostheses, and a method for producing spacers using said hollow mold or spacer casting mold.

Periprosthetic infections are a rare, but serious complication after insertion of hip, knee or other articular endoprostheses. In early infections manifesting within the first four weeks after the surgery (post-op.), it is often possible to keep the total articular endoprostheses (TEP) in place in the patient after the infection is cured. In late infections, though, it makes sense to remove the TEP in a one-stage or two-stage replacement operation and replace it with a revision TEP after surgical treatment. In the two-stage replacement operation, the infected TEP is removed first, then the infected tissue is subjected to debridement and subsequently the implant bed is filled with a spacer that is usually made of antibiotics-modified polymethylmethacrylate bone cement. The spacer replicates the shape of the TEP that has been removed and thus serves as a placeholder in the implant bed and thus prevents atrophy of the ligaments. To make the infection subside even more, antibiotics are released locally from the spacer into the surrounding tissue. Spacers usually stay in place in the patient for several weeks until the infection subsides. Then, a second surgery (operation) is used to remove the spacer and replace it with a cemented or non-cemented revision TEP.

A number of spacer casting molds for producing spacers during the operation have been proposed and all contain a given hollow space that is filled out with polymethylmethacrylate bone cement. The hollow molds for producing spacers according to U.S. Pat. No. 7,637,729, WO 98/51240, and U.S. Pat. No. 5,133,771 can be cited in this context for exemplary purposes. Injecting the polymethylmethacrylate bone cement dough into the hollow molds or spacer casting molds, the air must escape from the hollow space of the hollow mold through ventilation openings or ventilation channels.

This is disadvantageous in that ventilation of the hollow molds and/or spacer casting molds is difficult to achieve and, in some cases, residual air remains in corners and those regions that are not directly connected to ventilation channels. Another issue in this context is that the cement drives the air from the hollow mold outward through the ventilation channels during ventilation and spikes are thus generated in the ventilation channels. Said sharp, needle-like structures need to be removed by mechanical means before use of the spacers through sawing, polishing or cutting them off the spacer. Moreover, burs arise at the joints between the individual elements (such as half-shells) of the hollow molds while casting the bone cement and must be removed after the spacers are cured. Another issue in this context is that air inclusions may occur due to the forward motion of the cement while the bone cement is being filled in as a result of rolling motions of the cement dough at the inner surface of the spacer casting mold.

It is the object of the present invention to overcome these and other disadvantages that have not been specified above. In particular, a method for producing a spacer is to be provided, in which the formation of burs, spikes or other undesired projections needing to be removed after production and before insertion of the spacer is prevented as much as possible. Moreover, air inclusions in the fabricated spacers are to be minimized. It is also an object of the invention to provide a hollow mold for polymethylmethacrylate bone cement spacers that overcomes the known issues of current hollow molds. It shall be feasible to easily fill said hollow mold with polymethylmethacrylate bone cement using common vacuum cementing systems while mostly preventing air inclusions from being formed in order to avoid compromising the mechanical stability of the spacers through enclosed air bubbles. The formation of sharp, needle-like bone cement spikes in ventilation channels, known to occur in current commercial spacer casting molds, shall also be prevented. Moreover, the formation of sharp burs on the cured spacer of the type that is currently generated at the joints between the parts of the spacer casting mold shall be prevented. These are removed by mechanical means after curing of the polymethylmethacrylate bone cement through sawing or polishing in order to prevent injuring the patient. The hollow mold to be developed shall allow for the production of spacers that require no laborious mechanical post-processing. This is to save the medical user additional work during the surgery and lowers the cost of surgery as it reduces the surgery time.

Said objects are met through filling a cement into a compressed hollow space of a flexible compressed hollow mold, whereby the flexible hollow mold is expanded by the cement flowing into it, and the cement is filled into the hollow mold until the hollow space is expanded to a final state, whereby the hollow space in its final state determines the shape of the spacer to be produced, and the cement is then cured in said hollow space, and the spacer produced from the cement is removed from the hollow mold after curing.

The hollow mold is compressed along with the hollow space since the walls of the hollow mold are thin. The expanded final state is preferably, but not necessarily, the state up to which the hollow space can maximally be expanded. It is theoretically feasible to over-extend the hollow mold. However, the spacer would then no longer have the desired shape. The expanded final state is therefore the one, in which the internal shape of the hollow space is a negative duplicate of the spacer to be fabricated.

The invention can provide for the use, as cement, of a bone cement in this context, in particular comprising at least one antibiotic, preferably a polymethylmethacrylate bone cement.

Said cements are particularly well-suited for fabrication of spacers and possess the suitable flow properties for implementation of the method.

The invention can just as well provide the cement to fill up, preferably completely fill up, the hollow space in the expanded final state.

The hollow space being filled up prevents air or gas inclusions in the cement and thus in the spacer to be generated. This attains higher spacer stability.

Moreover, the invention can provide the cement to be filled into the hollow space through a filling opening, preferably to be injected and/or aspirated through the restoring force of the non-expanded hollow mold.

The effects of the injection or aspiration of the cement into the hollow mold through a defined and dedicated filling opening is that the hollow mold is filled up completely. Simultaneously, the surface generated through the filling opening can be situated at a location at which it matches the spacer or is particularly easy to process or does not interfere. This simplifies the production procedure further.

The invention can just as well provide the hollow mold to comprise a flexible material or to be made of a flexible material, whereby it is preferred to use as flexible material a plastic material, particularly preferably a metal-coated plastic material, a thermoplastic material, a thermoplastic elastomer and/or a silicone rubber, whereby the plastic hollow mold is produced, in particular, through blow molding.

Flexible materials, in particular flexible plastic materials, ensure that the hollow mold can be compressed particularly easily and simply. Moreover, the production from said materials is easy and inexpensive to implement.

According to a particularly preferred embodiment, the invention provides the hollow mold to be opened, preferably ripped open, along a pre-determined breakage site to allow the cured spacer to be removed.

The use of said pre-determined breakage sites simplifies the removal of the cured spacer and thus the implementation of methods according to the invention.

A particularly preferred method according to the invention can provide the hollow mold to be evacuated and to be compressed in the process before the cement is being filled in, whereby it is preferable that a valve is closed after evacuation such that the hollow space is being sealed and compressed, and that the valve is opened to allow the cement to be filled in.

The amount of air in the hollow mold is reduced through the evacuation and this reduces the number and size of possible inclusions.

The invention can just as well provide the hollow mold to be kept in the compressed state by means of a support means, such as, for example, a brace or a constriction.

Having the support means ensures that the hollow mold does not expand inadvertently even if the restoring force is large. The support means is released prior to or for filling the hollow mold with the cement.

Moreover, the invention can provide the compressed hollow space to account for a volume of less than 10% of the volume of the hollow space in the expanded final state, preferably of less than 3%, particularly preferably of less than 1% and/or the gas pressure in the compressed hollow space to be set to less than 10 kPa, preferably to less than 1 kPa, particularly preferably to less than 100 Pa.

At said volume reductions and/or gas pressures, it is feasible to attain sufficient reduction of the air or gas inclusions for the production of stable and high quality spacers.

The objects, on which the invention is based, are also met through a hollow mold for producing a spacer for insertion as a placeholder for an articular endoprosthesis, in particular for implementation of a method according to the invention, whereby the hollow mold is flexible and comprises a compressible hollow space, whereby the hollow space in the expanded final state defines the external shape of the spacer and the hollow mold comprises at least one filling opening through which a cement can be filled into the hollow space.

In this context, the invention can provide a valve element to be arranged at the filling opening, preferably a rotary valve having a roller-shaped rotating element or a hose with a hose clamp, whereby the closed valve element preferably seals the hollow space in gas-tight manner such that a vacuum can be maintained inside the hollow space.

The valve element renders the hollow mold according to the invention easy to operate. Moreover, this also ensures that the vacuum in the hollow space is maintained until the cement is filled in even if elastic materials are used.

The invention can just as well provide the hollow mold to consist of a plastic material, in particular a metal-coated plastic material, a thermoplastic material, a thermoplastic elastomer and/or a silicone rubber, whereby the plastic material preferably is transparent and/or remains stable for at least 10 minutes up to a temperature of 100° C.

Moreover, the invention can provide the hollow space in its expanded final state to replicate the external shape of a knee joint, hip joint, elbow joint, shoulder joint, endoprosthesis of said joints or parts of the joints or endoprosthesis thereof.

Said joints are treated with articular endoprostheses most frequently. Spacers in said shapes are therefore particularly well-suited.

The invention can just as well provide the hollow mold as a single part.

Moreover, the invention can provide the hollow mold to be a spacer hollow mold.

Having a single-part hollow mold prevents burs from being formed on the spacer generated, which then also do not need to be removed. Provision as spacer hollow mold is particularly well-suited for the production of spacers. A spacer casting mold is a spacer hollow mold.

The invention can just as well provide the wall of the hollow mold to comprise at least one predetermined breakage site which preferably should have a length corresponding to at least half of the circumference of the hollow mold, whereby the breakage site preferably has a length corresponding to the entire circumference of the hollow mold.

Using the pre-determined breakage site simplifies the removal of the cured spacer from the hollow mold.

According to the invention, a hollow mold for producing bone cement spacers can be made up of a flexible plastic hollow body containing a hollow space, which in its expanded state forms a negative duplicate of the spacer, at least one filling opening in the plastic hollow body that is connected to the hollow space, whereby the hollow space in the non-filled, non-expanded state has a volume corresponding to less than 10% by volume of the expanded hollow space, preferably has a volume corresponding to less than 5% by volume, particularly preferably less than 1% by volume of the expanded hollow space.

The invention is based on the surprising finding that there is no need to produce spacers through the use of rigid preforms, but that said spacers can just as well be produced by filling a cement into flexible hollow molds. Since said flexible hollow molds can be compressed, gas or air inclusions in the spacer can be prevented and no spikes are generated at the ventilation openings. Moreover, said flexible hollow molds are easy to implement as a single part. This dispenses with burs at spacer locations at which the individual parts of the spacer mold are put together. Since there are no spikes and burs, laborious post-processing of the spacer after the cement is cured can be avoided.

The invention provides a single-part flexible hollow mold that is present in the non-expanded state and contains only very little or no air or gas before being filled with polymethylmethacrylate bone cement. Filling-in the polymethylmethacrylate bone cement, the cement dough expands the hollow mold without any substantial amounts of air or gas having to be displaced from the hollow mold. Therefore, there is no need to have ventilation channels present which might form undesired spikes. Moreover, there is no bur formation since this concerns a single-part device. It is feasible just as well to fabricate the hollow mold from an elastic material possessing a high restoring force. By this means, the restoring force of the hollow mold can be used to aspirate the cement dough into the hollow mold starting from the non-expanded state that can be reached through compression or pushing together or by means of a mechanical fixation facility. However, the maximal expansion of the hollow mold needs to be restricted through, for example, a rigid external mesh restricting the maximal expansion of the hollow mold. This serves to ensure that the plastic hollow body does not expand due to the pressure of the cement dough when the cement dough is injected.

A central advantage of the invention is that the hollow mold can be provided as a single part. Consequently, there are no seams at the hollow mold and therefore no burs on the spacers produced in said single-part plastic hollow bodies.

The scope of the invention also includes the hollow mold to preferably have been made or be made through blow molding. Blow molding allows very different plastic materials to be formed into single-part seamless form bodies. It is particularly advantageous that blow molding is a simple technical process and can be carried out inexpensively with low tool expenses.

The scope of the invention also includes a valve element being arranged at the filling opening, if applicable, whereby a rotary valve having a roller-shaped rotating element is preferred. Having a valve function allows the hollow space to be protected from inadvertent ingress of air. This function is important especially when the restoring force of the non-expanded hollow mold is very large. Actuating the valve function allows the hollow space to be filled, for example and preferably, only when the cementing device touches against the filling opening. Then the valve element can be opened to aspirate the cement dough into the plastic hollow body due to the restoring force of the elastic plastic material. The invention can just as well provide for a hose having a hose clamp to be used as valve element.

Moreover, the invention can provide the hollow space of the plastic hollow body to form a negative mold of spacers in the expanded state of the plastic hollow body, with the spacers replicating the shape and function of hip endoprostheses, knee endoprostheses, shoulder endoprostheses or elbow endoprostheses.

The scope of the invention can just as well include metal reinforcements in the form of rods, screws or meshes to be arranged in the hollow space of the hollow mold. These become enveloped by the cement dough during spacer production and reinforce the mechanical stability of the spacers after they are cured. This allows the mechanical stability of the spacers to be improved markedly.

Moreover, methods according to the invention for producing spacers can provide for, firstly, polymethylmethacrylate bone cement to be injected into the filling opening of the hollow mold, whereby the polymethylmethacrylate bone cement expands the plastic hollow body until the pre-determined shape of the hollow space is filled completely, followed by curing of the polymethylmethacrylate bone cement, followed by the hollow mold being ripped open along the predetermined breakage site, and then the spacer being removed. According to the invention, the hollow mold can be a spacer casting mold.

Another method according to the invention can provide for, firstly, polymethylmethacrylate bone cement dough to be aspirated into the filling opening of the hollow mold through the restoring force of the non-expanded hollow mold until the pre-determined shape of the hollow space is filled completely, followed by curing of the polymethylmethacrylate bone cement, followed by the hollow mold being ripped open along the pre-determined breakage site, and then the spacer being removed.

BRIEF DESCRIPTION OF THE DRAWINGS

Exemplary embodiments of the invention shall be illustrated in the following on the basis of two schematic figures, though without limiting the scope of the invention. In the figures:

FIG. 1 shows a schematic side view of a hollow mold 1 according to the invention in the expanded final state. Said state is reached through filling a bone cement into the hollow mold 1. The hollow mold 1 comprises a filling opening that opens into a hose 2 or tube 2. The inside of the hollow mold 1 can be evacuated and the bone cement can be filled into the hollow mold 1 through said filling opening and the hose 2 or tube 2.

Figure 1:
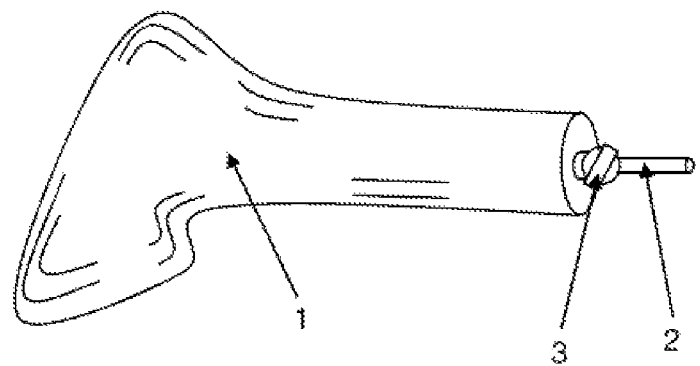
FIG. 1: shows a schematic side view of a hollow mold according to the invention containing a bone cement.
Figure 2:
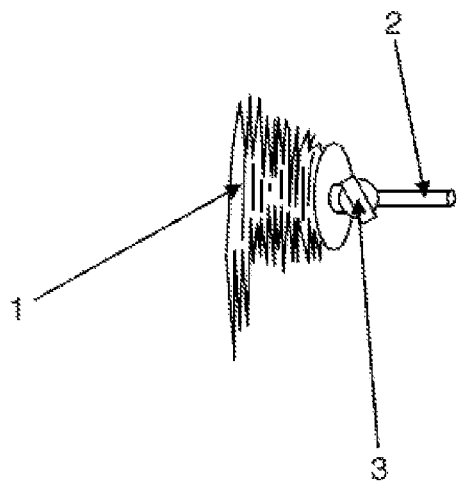
FIG. 2: shows a schematic side view of an evacuated hollow mold according to the invention.

In order to maintain the vacuum in the hollow mold 1 after evacuation of the hollow mold 1, a valve 3 is arranged in hose 2 or tube 2 at the filling opening. Said evacuated compressed state of the hollow mold 1 is shown in FIG. 2. The hollow mold 1 consists of a flexible plastic material and is produced through blow molding. If the hollow mold 1 is to be as non-elastic as possible, it is feasible, for example, to apply a layer of metal onto the plastic material or to use a plastic material that allows for as little plastic deformation as possible. The lack of elasticity ensures that the expanded final state of the hollow mold 1 and/or of the hollow space in the hollow mold 1 can be defined as exactly as possible and cannot be over-extended through injection of the bone cement and over-filling of the hollow mold 1. Alternatively, the external shape of the hollow mold 1 in the expanded final state can just as well be pre-determined through an external framework, a bracket or a brace.

If the hollow mold 1 has sufficient elasticity, the restoring force of the compressed and thus deformed hollow mold 1 can be utilized to aspirate bone cement through the filling opening into the hollow space of the hollow mold 1.

In the compressed shape, the volume inside the hollow space of the hollow mold 1 is displaced virtually completely, as is shown in FIG. 2. Moreover, the gas pressure inside the compressed hollow space is reduced markedly. In the compressed state, the hollow mold 1 is folded up. Folding is made feasible by the wall of the hollow mold 1 being flexible. For this purpose, the thickness of the wall is approximately 1 mm. As a matter of rule, the thickness of the walls must be matched to the rigidity of the material of which the hollow mold 1 is made. The aim is to have the hollow mold 1 fold up upon evacuation of the air from the hollow space of the hollow mold 1. However, this is jot to be associated with any irreversible plastic deformation of the hollow mold 1 in order to avoid pleats from forming undesired grooves on the surface of the spacer.

The features of the invention disclosed in the preceding description and in the claims, figures, and exemplary embodiments, can be essential for the implementation of the various embodiments of the invention both alone and in any combination.

LIST OF REFERENCE NUMBERS

1 Hollow body
2 Hose/tube
3 Valve

The invention claimed is:

1. A method for producing a spacer for insertion as a placeholder for an articular endoprosthesis, said method comprising:
   (1) filling a cement into a compressed hollow space of a compressed flexible hollow mold, whereby the flexible hollow mold is expanded by the cement flowing into it, and filling the cement into the hollow mold until the hollow space is expanded to a final state, whereby the hollow space in its final state determines the shape of the spacer to be produced, and then
   (2) curing the cement in said hollow space, and
   (3) removing from the hollow mold the spacer produced from the cement after curing,
   wherein:
   (i) the hollow mold is evacuated and compressed before the cement is being filled in, and a valve is closed after evacuation such that the hollow space is thereby sealed and compressed, and subsequently the valve is opened prior to step (1) to allow the cement to be filled in, and
   (ii) the compressed hollow space accounts for a volume of less than 10% of the volume of the hollow space in the expanded final state or the gas pressure in the compressed hollow space is set to less than 10 kPa.

2. Method according to claim 1, wherein the cement is a bone cement.

3. Method according to claim 1, wherein the cement completely fills up the hollow space in the expanded state.

4. Method according to claim 1, wherein the cement is filled into the hollow space through a filling opening.

5. Method according to claim 1, wherein the hollow mold comprises a flexible material or is made of a flexible material.

6. Method according to claim 1, wherein the hollow mold is opened along a pre-determined breakage site to allow the spacer to be removed.

7. Method according to claim 1, wherein the compressed hollow space accounts for a volume of less than 10% of the volume of the hollow space in the expanded final state and the gas pressure in the compressed hollow space is set to less than 10 kPa.

8. The method according to claim 2, wherein the cement is a bone cement which comprises at least one antibiotic.

* * * * *